(12) United States Patent
Sledz et al.

(10) Patent No.: US 11,737,815 B2
(45) Date of Patent: Aug. 29, 2023

(54) ABLATION AND MAPPING CATHETER FOR TREATMENTS IN ELECTROCARDIOLOGY

(71) Applicant: MEDINICE SPOLKA AKCYJNA, Kielce (PL)

(72) Inventors: Janusz Sledz, Skarzysko-Kamienna (PL); Sebastian Stec, Warsaw (PL)

(73) Assignee: Medinice Spolka Akcyjna, Kielce (PL)

( * ) Notice: Subject to any disclaimer, the term of this patent is extended or adjusted under 35 U.S.C. 154(b) by 502 days.

(21) Appl. No.: 15/566,679

(22) PCT Filed: Jun. 30, 2015

(86) PCT No.: PCT/PL2015/000106
§ 371 (c)(1),
(2) Date: Oct. 13, 2017

(87) PCT Pub. No.: WO2016/167673
PCT Pub. Date: Oct. 20, 2016

(65) Prior Publication Data
US 2018/0125574 A1  May 10, 2018

(30) Foreign Application Priority Data

Apr. 16, 2015 (PL) ........................................ 412047

(51) Int. Cl.
*A61B 18/14* (2006.01)
*A61B 18/12* (2006.01)
(Continued)

(52) U.S. Cl.
CPC .......... *A61B 18/1492* (2013.01); *A61B 5/287* (2021.01); *A61B 5/6852* (2013.01);
(Continued)

(58) Field of Classification Search
CPC . A61B 18/1492; A61B 18/1206; A61B 34/20; A61B 5/0422; A61B 5/6852;
(Continued)

(56) References Cited

U.S. PATENT DOCUMENTS 5,577,509 A * 11/1996 Panescu ............... A61B 5/0422
600/508
5,598,848 A * 2/1997 Swanson ............... A61B 5/0422
600/374
(Continued)

FOREIGN PATENT DOCUMENTS

EP        1112720 A1    7/2001
WO    2014012423 A1    1/2014

*Primary Examiner* — Tigist S Demie
(74) *Attorney, Agent, or Firm* — CRAFT CHU PLLC; Andrew W. Chu

(57) ABSTRACT

The ablation and mapping catheter dedicated to treatments in electrocardiology and ablation of cardiac arrhythmias with the possibility of visualisation includes a distal tip, diagnostic rings, a main tube, a guiding handgrip, and an electrical connector for a generator through which the diagnostic rings and a distal ring are connected to a system for three-dimensional electroanatomical mapping. The catheter includes at least 8 (up to 14) diagnostic rings, wherein 4 diagnostic distal rings are connected to one generator and through it to the system for three-dimensional electroanatomical mapping and to an electrophysiological system, and subsequent 4 (up to 10) diagnostic proximal rings are
(Continued)

connected to a second generator and/or to the system for three-dimensional electroanatomical mapping and to the electrophysiological system.

4 Claims, 3 Drawing Sheets

(51) Int. Cl.
  *A61B 5/00*    (2006.01)
  *A61B 34/20*   (2016.01)
  *A61B 5/287*   (2021.01)
  *A61B 17/00*   (2006.01)
  *A61B 18/00*   (2006.01)
  *A61B 34/10*   (2016.01)
  *A61B 90/00*   (2016.01)

(52) U.S. Cl.
  CPC .......... *A61B 18/1206* (2013.01); *A61B 34/20* (2016.02); *A61B 2017/00053* (2013.01); *A61B 2018/00005* (2013.01); *A61B 2018/00351* (2013.01); *A61B 2018/00577* (2013.01); *A61B 2018/00839* (2013.01); *A61B 2018/1273* (2013.01); *A61B 2018/1407* (2013.01); *A61B 2018/1467* (2013.01); *A61B 2034/105* (2016.02); *A61B 2034/107* (2016.02); *A61B 2034/2051* (2016.02); *A61B 2034/2065* (2016.02); *A61B 2090/376* (2016.02); *A61B 2090/3966* (2016.02)

(58) Field of Classification Search
  CPC ........ A61B 5/6855; A61B 2017/00053; A61B 2018/00005; A61B 2018/00351; A61B 2018/00577; A61B 2018/1467
  See application file for complete search history.

(56) References Cited

U.S. PATENT DOCUMENTS

| | | | | |
|---|---|---|---|---|
| 5,617,854 | A * | 4/1997 | Munsif | A61B 18/1492 600/374 |
| 5,908,445 | A * | 6/1999 | Whayne | A61B 1/00082 600/466 |
| 6,171,306 | B1 | 1/2001 | Swanson | |
| 2002/0002329 | A1 | 1/2002 | Avitall | |
| 2003/0009095 | A1* | 1/2003 | Skarda | C22C 14/00 600/374 |
| 2004/0059327 | A1 | 3/2004 | Jenkins | |
| 2004/0143254 | A1 | 7/2004 | Vanney | |
| 2006/0247522 | A1 | 11/2006 | McGee | |
| 2009/0209950 | A1 | 8/2009 | Starksen | |
| 2010/0057072 | A1* | 3/2010 | Roman | A61B 18/1492 606/33 |
| 2012/0035539 | A1 | 2/2012 | Tegg | |
| 2012/0203169 | A1* | 8/2012 | Tegg | B29C 65/02 604/95.04 |
| 2014/0316407 | A1* | 10/2014 | Stangenes | A61B 18/1492 606/41 |

* cited by examiner

ABLATION AND MAPPING CATHETER FOR TREATMENTS IN ELECTROCARDIOLOGY

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The object of the invention is an ablation and mapping catheter used for treatments in electrocardiology, comprising at least 8 diagnostic rings, wherein all the mapping stimulating rings are connected via connectors to a generator (generators) and allow a non-fluoroscopic mapping in a three-dimensional electroanatomical system. The diagnostic rings are evenly distributed at the distal end of an electrode. The rings allow controlling the shape of the electrode in the area of its bending in three-dimensional electroanatomical systems for navigation without X-radiation.

2. Description of Related Art Including Information Disclosed Under 37 CFR 1.97 and 37 CFR 1.98

An ablation catheter is known from the prior art US2004143254A, comprising a catheter tube which comprises proximal and distal parts, wherein the distal part is adapted to be placed in the body cavity, having tissues, to be ablated and is removed remotely from the said proximal part, wherein the distal part comprises flattened outer circumferential walls having an active area, wherein the said outer part has a cross-sectional shape along the active area, and in which this configuration is adapted to press the said active area against the tissue subjected to ablation. The catheter also comprises a lumen which is located in the active area, characterised in that at least one illuminator is located in the active area; and a porous tube is positioned within a duct and has at least one opening.

US2012035539A is also known, which relates to an electrode assembly of a catheter comprising an electrode tip which has further and closer end parts; and a multi-segment positioning magnet placed near the tip of an electrode. The electrode tip also comprises an ablation surface in the distal tip of the electrode.

Document US2004059327A relates to a contact detection system comprising: a catheter comprising a body having a closer end and a further end; an electrode comprising a tip and a base part; and an optical sensor, wherein the basic part of the electrode comprises an optically interactive surface; a part of the electrode is connected to the further end of the catheter; and the optical sensor is spaced from and operatively cooperates with the optically interactive surface. The optical sensor is configured to send and receive light energy or a signal based on light.

A known solution US2006247522A describes a magnetic mechanical navigation system for a catheter, comprising: a catheter comprising an elongated, flexible catheter body which has a distal end, at least a part which is adapted to be mechanically activated to adopt a curved geometry, a magnetically-responsive element realised at the distal end of the catheter; and an operating element at the distal end of the catheter. The magnetic navigation system is configured for applying a magnetic force of the magnetic element for deflecting the distal end of the catheter. The catheter comprises an operating element in the form of an ablation element. The operating element can be a diagnostic element.

A catheter known from U.S. Pat. No. 6,171,306 comprises a catheter body comprising a curved area shaped to at least partially enclose a tissue area, at least two spaced ablation electrodes in the curved area of the catheter body, positioned opposite each other, wherein the examined tissue is located between them, and any part of the electrode does not pass through the tissue; an indifferent electrode, a source of radio frequency energy in combination with ablation electrodes and an indifferent electrode, wherein respective sizes and arrangement of the at least two electrodes is such that a substantially continuous change is formed by the tissue area between the ablation electrodes in response to the simultaneous transmission from the ablation electrode to the tissue area to the indifferent electrode.

From WO1412423, a device is known which comprises an elongated tube comprising a closer end and a further end; an expandable system configured for transition from a radially folded state to a radially expanded state; a flexible printed circuit board (PCB flex); a number of electronic elements connected to PCB and configured to receive or transmit electrical signals. Document US2002002329A describes a recording and ablation catheter for electrically recording or mapping and creating lesions of linear ablations in the ventricle, comprising: a hollow vascular catheter or a casing, having a lumen for placing within the catheter: a guiding element for assisting in the navigation of the said catheter or casing into the vascular system of the patient: a flexible internal catheter which comprises a catheter operating point, having closer and further ends adapted to assume an arched shape, capable of contacting the inner surface of the ventricle, when used from the main catheter or casing through an internal duct on which there is the said operating part of the catheter and a number of spaced electrodes connected in series on the said operating section of the catheter.

None of the known solutions indicates the need for better visibility of the catheter position in the human body, and especially the one realised by means of diagnostic rings arranged on a distal section of the catheter, longer than usual, limited to 3-4 cm.

The existing ablation catheters have standard 4 diagnostic rings connected to a generator and through additional connections therefrom to an electrophysiological system and/or a three-dimensional electroanatomical system. The first distal ring is also an ablation ring, and its width and structure depends on the manufacturer and the type of electrode. By default, generators do not comprise connectors for more than 4 rings of the point ablation electrode. Introduction of additional rings allows for the reception of signals from the distal part, i.e. about 4 cm, as well as from an electrode part distant from the distal end at a distance of above 4-10 cm. This allows for the reception of signals from two areas of the heart simultaneously—e.g. from the right ventricle, the His-bundle area and the right atrium. This will allow for simplified diagnostics with one electrode analysing simultaneously atrio-ventricular and ventriculo-atrial conductions and the His-bundle area. The additional rings can be used for specialised differentiating stimulations and stimulations on demand while performing mapping or ablation from the distal ring of the catheter. The additional rings will be visible in three-dimensional electroanatomical systems, in particular in the range of the electrode bending, which will allow for the visualisation of the electrode curvature and its shape at a distance of above 8-10 cm, and not only about 4 cm.

BRIEF SUMMARY OF THE INVENTION

The present solution consists in placing, in the area of the distal tip of the catheter, an additional quantity of diagnostic rings allowing, above all, the navigation by means of a system for three-dimensional electroanatomical mapping, the faster collection of potentials for creating virtual maps of heart cavities, and the catheter visibility in the area of its bending in the treatments without or with very significant reduction of the need to use X-radiation. The present solution provides the operator with new and useful capabilities.

Modern standards for treating arrhythmia assume an early qualification of children and adults with recurrent arrhythmia resistant to pharmacological treatment for ablation, as well as treatments for the prevention of occurrence of another attack of arrhythmia or removal of additional atrioventricular pathways. An invasive diagnostic method performed before and after the ablation treatment is an invasive electrophysiology study using diagnostic catheters. It consists in the analysis of parameters of stimulus formation, conduction and intracardiac potentials in the atria, the conduction system and in the ventricles. Modern electrophysiology aims at reducing the invasiveness and the complexity of treatments with the reduction of the number of electrodes, vascular punctures, and patient and medical personnel exposure to adverse effects of X-radiation (risk of cancer, encumbrance of outfits and discomfort of radiological protection).

The essence of the invention is an ablation and mapping catheter for treatments in electrocardiology, comprising a distal tip, diagnostic rings, a main tube, a guiding handgrip, an electrical connector for a generator through which the diagnostic rings and a distal ring are connected to a system for three-dimensional electroanatomical mapping and to an electrophysiological system, characterised in that it comprises at least 8 diagnostic rings, wherein 4 diagnostic distal rings (3b) are connected to one generator and through it to the system for three-dimensional electroanatomical mapping, and subsequent at least 4 (up to 10) diagnostic proximal rings (3a) are connected to a second generator and/or to the system for three-dimensional electroanatomical mapping.

Preferably, the ablation and mapping catheter comprises up to 14 diagnostic rings, wherein 4 rings are constituted by the diagnostic distal rings (3b), and at least 4 (up to 10) rings are constituted by the diagnostic proximal rings (3a).

Preferably, the main tube (2) is terminated by the distal ring (1).

Preferably, the distal ring (1) has smooth, rounded, atraumatic edges.

Preferably, the ablation and mapping catheter can be guided and monitored by the system for three-dimensional electroanatomical mapping with visualisation of the shape of the distal part of the catheter tip with the area of its bending.

Preferably, the main tube (2) in the guiding handgrip (5) is separated into two wiring harnesses (6 and 8) and a harness (7) for cooling the distal ablation ring of the catheter.

The ablation and mapping catheter is a universal type of catheter for ablation, stimulation, diagnosis and which allows for navigation without the use of X-ray fluoroscopy in the three-dimensional electroanatomical system. It comprises at least 8-14 diagnostic rings allowing for visualisation of the distal section having over a dozen centimetres of the catheter and of its bending.

An advantage of the catheter according to the invention is an increased number of diagnostic rings present behind the distal area of 4 cm and beyond the distal bending of the electrode, allowing for visualisation of the distal section of the electrode, having 8 to 14 cm, in the three-dimensional electroanatomical system. This allows the analysis of the shape of the distal end of the electrode, of deformations of the distal bending, and of the risk assessment for the looping of the distal end of the electrode when passing through vessels and cardiac cavities. Another advantage is the use of dimensions (diameter width) of 4 to 8 F allowing for the production of the catheter of very small sizes of diameter, useful in the treatment of children and young people and those with low body weight (Size of the catheter is given in French (F) scale which specifies the perimeter of the catheter in millimetres. Conversion of this size to the diameter of the catheter is as follows IF=0.33 mm).

An advantage of the catheter is the possibility of using, from one ablation catheter, stimulation, recording of potentials and navigation without the use of X-ray fluoroscopy from more than 4 rings. This allows, when using one electrode, for performing simultaneous and improved mapping, stimulation, analysis of potentials and formation of electroanatomical maps from at least 2 heart cavities and to reduce the need to use additional diagnostic catheters and additional punctures. Increasing the number of rings by additional 4-10 ones on the distal section of the catheter, including its bending, is a unique solution and allows for visualisation of a substantially longer section in a three-dimensional electroanatomical system for non-fluoroscopic mapping and navigation (without X-radiation), which will ensure a constant monitoring of not only the catheter tip (4 cm), but also the distal part of the catheter and its bending distanced by 4-10 cm from the catheter end. This will allow for an accurate estimation of the catheter position, its deformations and curvature, which may improve efficiency and precision in the navigation of the catheter. The project of the catheter was created based on experiences and demand of electrophysiologists conducting ablation treatments in the three-dimensional non-fluoroscopic system and on limitations in introducing the protocol of non-fluoroscopic navigation, visualisation and ablation of arrhythmia in children and adolescents.

From the handgrip, two electrical connections extend which connect to an electrical outlet connectable to a connector for transmitting parameters to the electroanatomical and electrophysiological systems. From the handgrip, when using a system for cooling the electrode tip, a connector extends which is used for cooling the distal tip and the distal ring implementing current applications, the said connector not being a part of the invention. In addition, the handgrip comprises a system for guiding the distal tip of the catheter, which is not part of the invention either.

BRIEF DESCRIPTION OF THE SEVERAL VIEWS OF THE DRAWINGS

The ablation and mapping catheter according to the invention has been further described in embodiments and in the drawings.

DETAILED DESCRIPTION OF THE INVENTION

Figure 1:
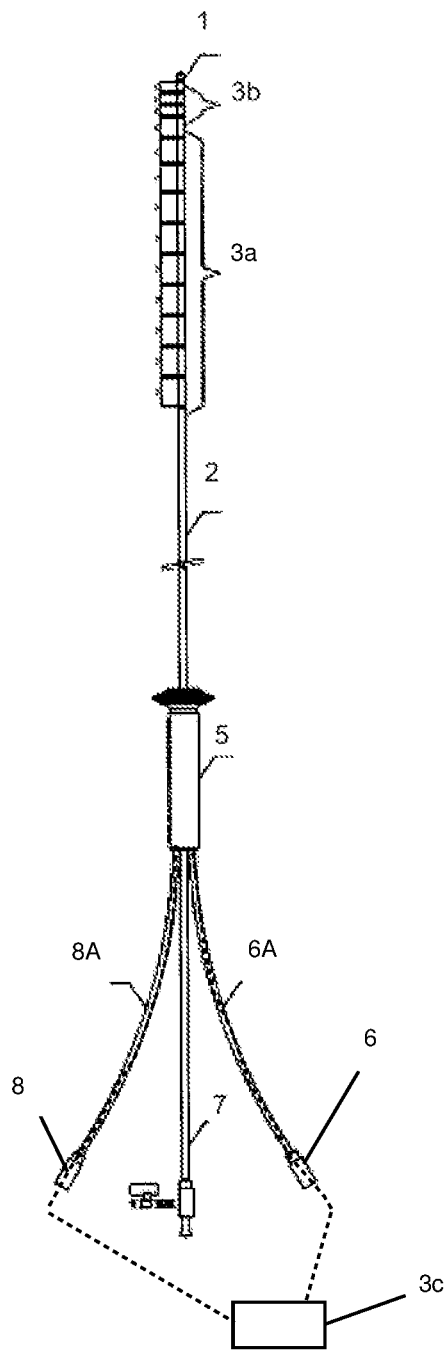
FIG. 1 shows a top view of the ablation and mapping catheter together with a guiding handgrip and functional connectors.
Figure 2:
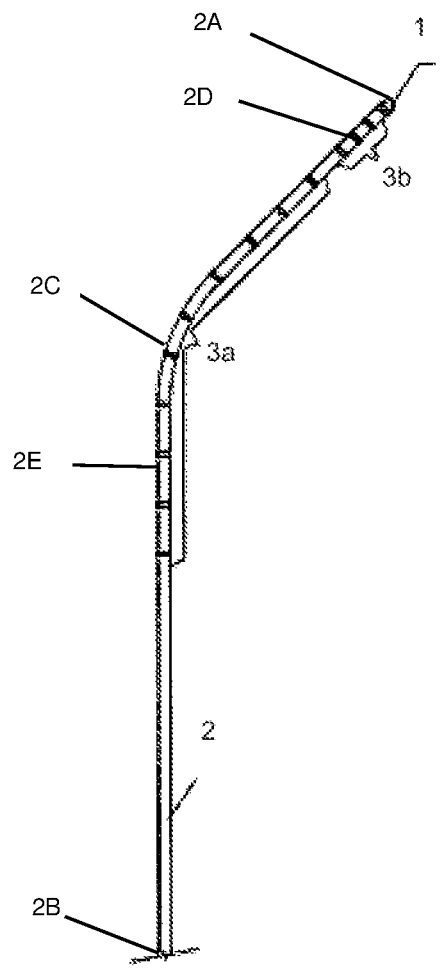
FIG. 2 shows a top view of a main tube including a distal ring and diagnostic rings.
Figure 3:
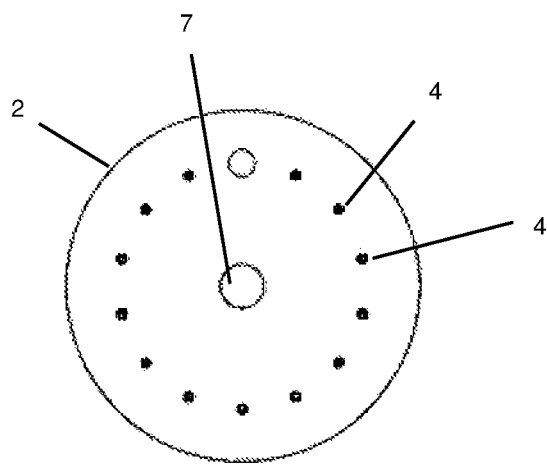
FIG. 3 shows a cross sectional view through the main tube of the ablation and mapping catheter.

The ablation and mapping catheter comprises a guiding handgrip 5, a main tube 2 having a distal end 2A, a proximal end 2B, and a bend portion 2C between the distal end and the proximal end (FIG. 2), a distal ring 1, diagnostic rings 3a,3b, including distal or a first plurality 3b and proximal or a second plurality 3a ones and two electrical connectors 6 and 8 (a first electrical connector 6, and a second electrical connector 8) for electric wires 4 connecting the diagnostic rings 3a and 3b and the distal ring 1 to an electrophysiological system 3c. Furthermore, the catheter comprises a connector for a cooling duct 7, which is not an object of the invention.

The ablation and mapping catheter comprises at least 8 diagnostic rings, wherein at least 4 rings are connected to one generator or first electrical connector 6 and through it to a three-dimensional system 3c, and subsequent 4-10 ones are connected to a second generator or second electrical connector 8 and/or further through it to the three-dimensional system 3c.

In addition, in the main tube 2, there are wires 4 for guiding the distal end of the catheter and a duct 7 for liquid for cooling the distal ablation ring or distal ring 1 of the ablation catheter, wherein they are not an object of the invention.

The proximal end of the main tube, when connecting to the guiding handgrip, is separated into two wiring harnesses and a harness which is provided with a tap and a tip for cooling the distal ablation ring 1 of the catheter.

The distal ring of the catheter has an atraumatic shape, which means it has a smooth, rounded tip with openings allowing for cooling of the electrode. Sharp edges would disrupt the continuity of vessels and increase the risk of perforations.

The ablation and mapping catheter comprises diagnostic rings for the analysis of electrical parameters of the heart and vessels, present in an amount of 8 to 14 units (3a and 3b—4 by default) distributed evenly over the length of 4 to 14 cm. These rings are located near the distal end of the catheter. In a preferred embodiment, the diagnostic rings serve as rings visible under X-rays and in the system for non-fluoroscopic navigation and mapping. The diagnostic rings are located before, on and behind the distal tip of the catheter. In the known point ablation catheters, (ablation from one ring) rings were not placed in the area behind the bending of the distal part of the catheter and at a considerable distance from the distal ring. In addition, for point ablations, not more than 4 rings were used for connecting to a power generator of radio frequency.

In the area of the proximal end of the main tube, there is the guiding handgrip within which electrical wires are being separated. The separation of the electrical wires allows, apart from a standard connector for 4 diagnostic distal rings (3b), the use of an additional connection for subsequent diagnostic proximal rings (3a).

The ablation and mapping catheter is made of an elastic material allowing it to be easily bent, and the distal end is provided with a guiding system located in the handgrip of the catheter and connected with appropriate bands.

The catheter is ultimately positioned by the non-fluoroscopic three-dimensional electroanatomical system or/and by means of the navigation with the use of X-radiation.

The ablation and mapping catheter is introduced into venous or arterial peripheral vessels (femoral vein/artery) of the patient and is then guided through main vessels into right and left cavities of the heart. The guiding system allows for bending the distal tip of the catheter. Navigation and localisation of the catheter position can be conducted based on the catheter translucency under X-radiation or based on analysis of potentials and electrophysiological parameters through the three-dimensional system and the non-fluoroscopic navigation (without X-radiation). The catheter, thanks to all the diagnostic rings (1, 3 a, 3 b), allows a continuous recording of potentials and of the construction of virtual electroanatomical map forming an image of the examined veins, arteries and heart cavities. At the time when the operator reaches his goal, i.e. reaches the ablation location or the desired location in which an ablation treatment from the distal ring 1 is to be conducted, application of radio frequency current is conducted with the use of a system for cooling the electrode tip.

The diagnostic rings (1, 3a, 3b) allow for the recording of electrophysiological parameters (shape and amplitude of unipolar and bipolar electric potential, impedance), the selective stimulation with an external stimulator, and the non-fluoroscopic navigation using the three-dimensional system. The operator, thanks to additional proximal rings 3a on a second portion 2E of the main tube 2 between the bend portion and the proximal end with second orientation independent from the bend portion, has the ability to quickly and simultaneously record potentials and to stimulate from places distant from the distal ring 1 and is able to assess the shape of bending, looping and deformations of the distal part of the catheter on a first portion 2D of the main tube 2 between the distal end and the bend portion with a first orientation set by the bend portion. The operator, thanks to additional proximal rings 3a, has the ability, without changing the position of the distal tip of the electrode, to conduct control stimulations and monitoring from distant areas or other cavities of the heart without changing the position of the catheter. After mapping, stimulation of the ablation, the catheter in its entirety is removed by a sheath passage (introducer). The sheath passage is removed according to the adopted protocol depending on the degree of anticoagulation in the patient during the treatment.

We claim:

1. An ablation and mapping catheter for treatments in electrocardiology, the catheter comprising:
   a main tube having a distal end, a proximal end, and a bend portion having a single bend and being between said distal end and said proximal end;
   a guiding handgrip on said main tube and adjacent said proximal end;

a first plurality of at least four diagnostic rings positioned on a first portion of said main tube between said distal end and said bend portion so as to map a first area of a heart, said first portion having a first orientation set by said bend portion, wherein said first plurality of at least four diagnostic rings is comprised of a distal ring, said distal ring being positioned at said distal end of said main tube furthest from said bend portion;

a second plurality of at least four diagnostic rings positioned on a second portion of said main tube between said bend portion and said proximal end so as to map a second area of the heart, said second portion having a second orientation, said second orientation being independent from said bend portion so as to reach desired location for an ablation treatment by said distal ring of said first plurality of at least four diagnostic rings relative to said single bend and said second orientation;

a first electrical connector being connected to said first plurality of at least four distal diagnostic rings;

a second electrical connector being connected to said second plurality of at least four proximal diagnostic rings;

a system for three-dimensional electroanatomical mapping in communication with said first plurality of at least four distal diagnostic rings through said first electrical connector and said second plurality of at least four proximal diagnostic rings through said second electrical connector so as to constantly monitor said first area of the heart through said first portion and said second area of the heart through said second portion according to said second orientation relative to said bend portion;

a first channel connected to said main tube at said guiding handgrip;

a second channel connected to said main tube at said guiding handgrip; and a cooling duct connected to said main tube at said guiding handgrip, wherein said first electrical connector extends through said first channel, and wherein said second electrical connector extends through said second channel.

2. The ablation and mapping catheter, according to claim 1, wherein said distal ring has smooth, rounded, atraumatic edges.

3. A spot ablation and mapping catheter for treatments in electrocardiology, the catheter comprising:

a main tube having a distal end, a proximal end, and a bend portion between said distal end and said proximal end;

a guiding handgrip on said main tube and adjacent said proximal end;

a first plurality of at least four diagnostic rings positioned on a first portion of said main tube between said distal end and said bend portion so as to map a first area of a heart, said first portion having a first orientation set by said bend portion, wherein said first plurality of at least four diagnostic rings is comprised of a distal ablation ring, said distal ablation ring being positioned at said distal end of said main tube furthest from said bend portion so as to determine an ablation location;

a second plurality of at least four diagnostic rings positioned on a second portion of said main tube between said bend portion and said proximal end so as to map a second area of the heart, said second portion having a second orientation, said second orientation being independent from said bend portion so as to reach said ablation location with said distal ring of said first plurality of at least four diagnostic rings relative to said single bend and said second orientation, wherein a portion of said first plurality of at least four diagnostic rings are between said ablation location and said bend portion;

a first electrical connector being connected to said first plurality of at least four distal diagnostic rings;

a second electrical connector being connected to said second plurality of at least four proximal diagnostic rings;

a system for three-dimensional electroanatomical mapping in communication with said first plurality of at least four distal diagnostic rings through said first electrical connector and said second plurality of at least four proximal diagnostic rings through said second electrical connector so as to constantly monitor said first area of the heart through said first portion and said second area of the heart through said second portion according to said second orientation relative to said bend portion;

a first channel connected to said main tube at said guiding handgrip;

a second channel connected to said main tube at said guiding handgrip; and a cooling duct connected to said main tube at said guiding handgrip, wherein said first electrical connector extends through said first channel, and wherein said second electrical connector extends through said second channel.

4. The spot ablation and mapping catheter, according to claim 3, wherein said distal ablation ring has smooth, rounded, atraumatic edges.

* * * * *